(12) United States Patent
Tegg et al.

(10) Patent No.: US 10,821,266 B2
(45) Date of Patent: *Nov. 3, 2020

(54) MEDICAL DEVICE WITH A NESTED LAP JOINT AND A FUSED CONDUCTIVE ELEMENT AND METHOD FOR FABRICATING THE SAME

(71) Applicant: ST. JUDE MEDICAL, CARDIOLOGY DIVISION, INC., St. Paul, MN (US)

(72) Inventors: Troy T. Tegg, Elk River, MN (US); Alexander C. Houck, Hopkins, MN (US); Salome Arias-Gonzalez, Maple Grove, MN (US); John S. Her, Brooklyn Park, MN (US); Somally Mom, Savage, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 44 days.

This patent is subject to a terminal disclaimer.

(21) Appl. No.: 15/987,597

(22) Filed: May 23, 2018

(65) Prior Publication Data

US 2018/0333561 A1 Nov. 22, 2018

Related U.S. Application Data

(63) Continuation of application No. 14/724,119, filed on May 28, 2015, now Pat. No. 10,166,367.

(Continued)

(51) Int. Cl.
*A61M 25/01* (2006.01)
*A61B 18/14* (2006.01)
(Continued)

(52) U.S. Cl.
CPC ........... *A61M 25/0147* (2013.01); *A61B 5/04* (2013.01); *A61B 18/1492* (2013.01);
(Continued)

(58) Field of Classification Search
CPC .............. A61B 18/1492; A61B 18/201; A61B 2017/00044; A61B 2017/00526;
(Continued)

(56) References Cited

U.S. PATENT DOCUMENTS 5,150,702 A 9/1992 Miyanaga et al.
5,160,559 A 11/1992 Scovil
(Continued)

FOREIGN PATENT DOCUMENTS

EP 0980693 A1 2/2000
JP H09201367 A 8/1997
(Continued)

*Primary Examiner* — Brandy S Lee
(74) *Attorney, Agent, or Firm* — Dykema Gossett PLLC

(57) ABSTRACT

A medical device for the diagnosis or treatment of tissue in a body and method for fabricating the same are provided. The device includes comprises a first shaft and a second shaft. The first shaft includes a longitudinal axis, and the second shaft includes a second shaft axial end disposed within the first shaft. The second shaft is connected to the first shaft by a first nested lap joint formed between the first shaft and the second shaft.

10 Claims, 12 Drawing Sheets

Related U.S. Application Data

(60) Provisional application No. 62/008,180, filed on Jun. 5, 2014.

(51) Int. Cl.
| | | |
|---|---|---|
| *A61M 25/00* | (2006.01) | |
| *A61B 5/04* | (2006.01) | |
| *A61B 5/00* | (2006.01) | |
| *A61B 17/00* | (2006.01) | |
| *A61B 18/00* | (2006.01) | |
| *A61B 18/20* | (2006.01) | |
| *A61B 18/02* | (2006.01) | |
| *A61B 5/01* | (2006.01) | |
| *A61B 5/042* | (2006.01) | |

(52) U.S. Cl.
CPC ...... *A61M 25/005* (2013.01); *A61M 25/0009* (2013.01); *A61M 25/0012* (2013.01); *A61M 25/0136* (2013.01); *A61M 25/0138* (2013.01); *A61M 25/0144* (2013.01); *A61B 5/01* (2013.01); *A61B 5/042* (2013.01); *A61B 5/6852* (2013.01); *A61B 18/201* (2013.01); *A61B 2017/00044* (2013.01); *A61B 2017/00526* (2013.01); *A61B 2018/0016* (2013.01); *A61B 2018/00071* (2013.01); *A61B 2018/00357* (2013.01); *A61B 2018/00821* (2013.01); *A61B 2018/00839* (2013.01); *A61B 2018/0212* (2013.01)

(58) Field of Classification Search
CPC .. A61B 2018/00071; A61B 2018/0016; A61B 2018/00357; A61B 2018/00821; A61B 2018/00839; A61B 2018/0212; A61B 5/01; A61B 5/04; A61B 5/042; A61B 5/6852; A61B 17/320068; A61M 25/0009; A61M 25/0012; A61M 25/005; A61M 25/0136; A61M 25/0138; A61M 25/0144; A61M 25/0147
See application file for complete search history.

(56) References Cited

U.S. PATENT DOCUMENTS

| | | |
|---|---|---|
| 5,662,622 A | 9/1997 | Gore |
| 6,187,130 B1 * | 2/2001 | Berard ............... B29C 66/0042 156/294 |
| 6,224,803 B1 | 5/2001 | Tiernan |
| 7,060,050 B2 | 6/2006 | Kliem et al. |
| 7,993,481 B2 | 8/2011 | Hastings et al. |
| 8,376,991 B2 | 2/2013 | Kauphusman et al. |
| 8,814,825 B2 | 8/2014 | Tegg et al. |
| 2004/0140585 A1 | 7/2004 | Sterud et al. |
| 2008/0004681 A1 | 1/2008 | Marshall |
| 2010/0217234 A1 | 8/2010 | Grovender et al. |
| 2011/0125134 A1 | 5/2011 | Schwager |
| 2012/0116429 A1 | 5/2012 | Levine et al. |
| 2013/0150808 A1 * | 6/2013 | Ogle ............... A61M 25/0012 604/264 |
| 2014/0135736 A1 | 5/2014 | Hebert |

FOREIGN PATENT DOCUMENTS

| | | |
|---|---|---|
| JP | 2002214540 A | 7/2002 |
| WO | 2011033783 A1 | 3/2011 |

\* cited by examiner

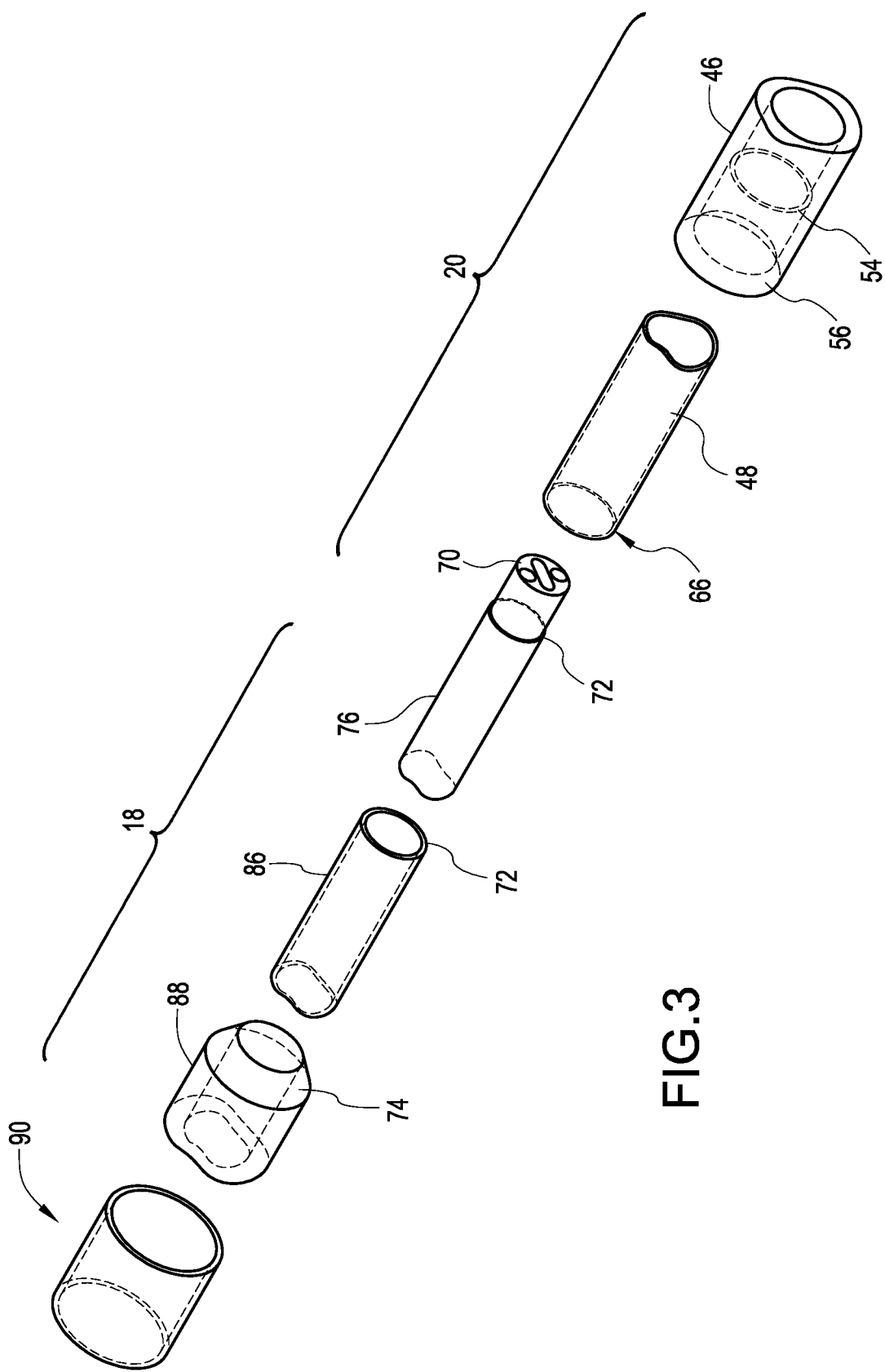

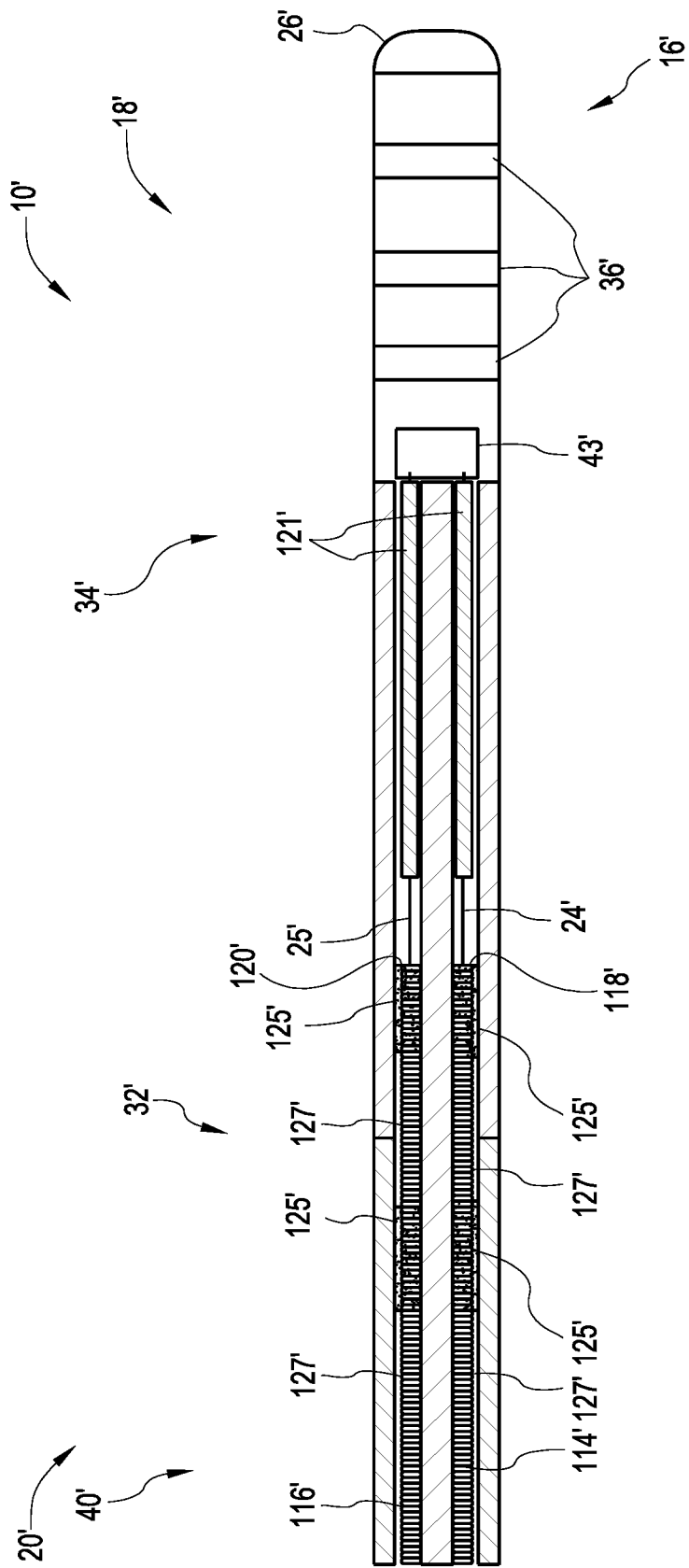

MEDICAL DEVICE WITH A NESTED LAP JOINT AND A FUSED CONDUCTIVE ELEMENT AND METHOD FOR FABRICATING THE SAME

CROSS-REFERENCE TO RELATED APPLICATIONS

This application is a continuation of U.S. patent application Ser. No. 14/724,119, filed 28 May 2015, which claims the benefit of U.S. provisional application No. 62/008,180, filed 5 Jun. 2014, both of which are hereby incorporated by reference as though fully set forth herein.

BACKGROUND a. Technical Field

This disclosure generally relates to a medical device for diagnosis or treatment of tissue in a body and method for fabricating the same. In particular, the instant disclosure relates to the joining of various members and/or components in shafts of a medical device.

b. Background Art

This background description is set forth below for the purpose of providing context only. Therefore, any aspects of this background description, to the extent that it does not otherwise qualify as prior art, is neither expressly nor impliedly admitted as prior art against the instant disclosure.

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

A catheter may be deployed and manipulated through a patient's vasculature to the intended site, for example, a site within a patient's heart or a chamber or vein thereof. The catheter may carry one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter may impart ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

To position a catheter within the body at a desired site, some type of navigation may be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to position the distal portion of the catheter during an electrophysiological procedure. The proximal end of the catheter can be manipulated to guide the catheter through a patient's vasculature. The distal tip can be deflected by a pull wire attached at the distal end of the catheter that extends to a control handle that controls the application of tension on the pull wire.

Two of the mechanical considerations for a catheter shaft are that it transmit torque and resist compression during use. Substantial frictional forces sometimes resist transmission of torque across the length of the catheter. In some cases, these forces can cause the catheter shaft to twist about a longitudinal axis of the catheter shaft, storing energy in the process in a spring-like fashion. If the energy is released suddenly, the distal end of the catheter, which may be deflected by a steering mechanism, can be undesirably propelled with significant force.

With respect to resisting compression during use, it is important for medical personnel to be able to advance the catheter through a vessel, sometimes against significant frictional resistance, without undue axial compression or snaking of the catheter shaft. Shaft compression can result in a loss of control for the medical practitioner and can complicate the positioning of the distal end of the catheter shaft at a desired location for a medical procedure. In addition, medical personnel may rely on tactile feedback to attain and verify proper positioning of the catheter, and such feedback can be impaired by excessive compressibility.

The foregoing discussion is intended only to illustrate the present field and should not be taken as a disavowal of claim scope.

SUMMARY

Among other things, various embodiments disclosed herein are directed to a medical device for diagnosis or treatment of tissue in a body and a method for fabricating the same. In particular, the instant disclosure relates to a medical device with a nested lap joint and a fused conductive element and method for fabricating the same.

A medical device for the diagnosis or treatment of tissue in a body in accordance with one embodiment of the present teachings includes a first shaft and a second shaft. The first shaft includes a longitudinal axis, and the second shaft includes a second shaft axial end disposed within the first shaft. The second shaft is connected to the first shaft by a first nested lap joint formed between the first shaft and the second shaft.

A medical device for the diagnosis or treatment of tissue in a body in accordance with another embodiment of the present teachings includes a first shaft, a second shaft, and a conductive element disposed within at least one of the first and second shafts. The second shaft is connected to the first shaft by a first nested lap joint formed between the first shaft and the second shaft.

A method for fabricating a medical device in accordance with another embodiment of the present teachings includes providing a shaft with a shaft inner surface. The method further includes providing a conductive element. The method further includes inserting the conductive element into the shaft. The method further includes fusing at least a portion of the conductive element to the shaft inner surface to form a fused area. Fusing at least a portion of the conductive element comprises selectively heating the portion of the conductive element using an energy source.

A medical device and method for making the same in accordance with the present teachings is advantageous relative to conventional devices and methods. A medical device and method for making the same in accordance with the present teachings provide a more reliable and durable medical device with less kinking and a reduced risk of joint separation by spreading the loads over the various layers of the device. In addition, the method for making the device allows for more precise embedding of the conductive element and increased efficiency, which results in a decrease in cost.

The foregoing and other aspects, features, details, utilities, and advantages of the present disclosure will be apparent from reading the following description and claims, and from reviewing the accompanying drawings.

BRIEF DESCRIPTION OF THE DRAWINGS

FIG. 3 is an exploded view of the portion of the medical device illustrated in FIG. 2 (with some components omitted for clarity).

FIG. 8B is a schematic view of a distal portion of the medical device of FIG. 1 in accordance with another embodiment of the present teachings.

DETAILED DESCRIPTION

Figure 1:
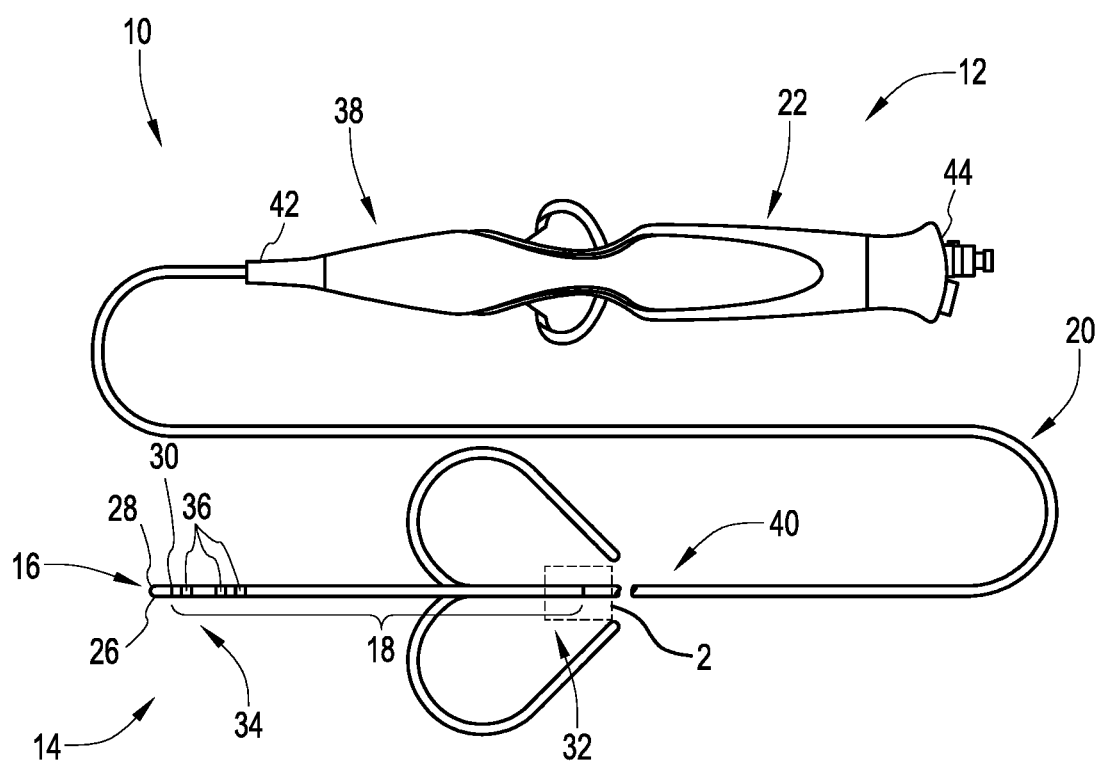
FIG. 1 is a schematic view of a medical device for diagnosis or treatment of tissue in a body in accordance with one embodiment of the present teachings.

An electrophysiology catheter may include an elongate proximal shaft portion and a deflectable distal shaft portion. The connection between the proximal and distal shaft portions must be sufficient enough to withstand tensile loads and other stresses. The proximal shaft portion may be relatively stiff, while the distal deflectable shaft portion may be relatively less stiff. When the connection or joint between the proximal and distal shaft portions transitions stiffness abruptly, the catheter may exhibit a non-uniform curvature during deflection and have inequitable stress profiles. However, a joint that transitions stiffness gradually across the catheter length may result in a catheter having uniform curvature and equitable stress profiles. Moreover, having multiple bonded layers in the catheter may result in even more gradual stiffness transitions. In addition, when using rigid adhesives, it may be desirable to spread the bond joints out (since the adhesive may be more rigid than the surrounding materials). However, if the bond joint with rigid adhesive is too long, the catheter may exhibit non-uniform curvature upon deflection or bending.

In order to provide the desired mechanical property of resisting compression during use, a catheter may further incorporate a compression coil and/or spring pack embedded within the catheter shaft, as discussed in greater detail in commonly owned co-pending U.S. patent application Ser. No. 13/838,124 filed Mar. 15, 2013 (hereinafter "the '124 Application"), which is hereby incorporated by reference in its entirety as though fully set forth herein. Components, such as compression coils and spring packs, can be embedded into the catheter by heating (and subsequently cooling) the outer layer(s) of the catheter surrounding the components, as discussed in greater detail in commonly owned U.S. Pat. No. 7,993,481 filed Dec. 28, 2006 (hereinafter "the '481 Patent"), which is hereby incorporated by reference in its entirety as though fully set forth herein.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of a medical device or instrument used to treat a patient. The term "proximal" refers to the portion of the device closest to the clinician (or to a robotic control configured to manipulate the device) and the term "distal" refers to the portion located furthest from the clinician. It will be further appreciated that for conciseness and clarity, spatial terms such as "vertical,"

"horizontal," "up," and "down" may be used herein with respect to the illustrated embodiments. However, medical devices may be used in many orientations and positions, and these terms are not intended to be limiting or absolute. Furthermore, the terms "bonded," "affixed," and "fused" as used herein are intended to mean the same thing.

Referring now to the drawings wherein like reference numerals are used to identify identical or similar components in the various views, FIG. 1 is a schematic view of a medical device 10 for diagnosis or treatment of tissue in a body in accordance with one embodiment of the present teachings. Device 10 is provided for examination, diagnosis, and treatment of internal body tissues. In accordance with one embodiment of the present teachings, device 10 comprises an electrophysiology ("EP") catheter. It should be understood that device 10 could be several types of EP catheters, such as a mapping catheter, an ablation catheter, and an intracardiac echocardiograph (ICE) catheter, and could use different types of energy (e.g., radio frequency (RF), cryoablation, ultrasound, laser, microwave, electroporation, etc.). Further, it should be understood that the present teachings can be used for other types of medical devices (and used in the diagnosis or treatment of tissue including, for example, introducer sheaths). Accordingly, one of ordinary skill in the art will recognize and appreciate that the medical device and method of fabricating the same disclosed herein can be used in any number of diagnostic and therapeutic applications. In its most general form, device 10 is generally cylindrical in shape with a proximal portion 12 and a distal portion 14 and comprises a tip assembly 16 at distal portion 14, a deflectable distal shaft 18 proximal to tip assembly 16, a proximal shaft 20 proximal to distal shaft 18, a handle assembly 22 at proximal portion 12, and pull wires 24, 25 (shown in FIGS. 4A-8B) extending from handle assembly 22 through proximal shaft 20 and distal shaft 18, in accordance with an embodiment.

Still referring to FIG. 1, tip assembly 16 may comprise a tip electrode 26 having a distal end 28 and a proximal end 30. Tip electrode 26 may be configured for various functions including, without limitation, an active outer surface that is configured for exposure to blood and/or tissue. Tip electrode 26 of tip assembly 16 may have an aperture (not shown) formed therein that is sufficiently sized and configured to receive a wire (not shown) that is connected to tip electrode 26. One end of the wire is connected to tip electrode 26 and another end is configured to be connected to, for example, monitoring, recording, or ablation devices, such as a radiofrequency (RF) generator. The wire may be a pre-coated wire that is insulated from other components in tip assembly 16. Tip electrode 26 of tip assembly 16 may further include another aperture (not shown) formed therein that is configured to receive a thermocouple (not shown). The thermocouple may be configured to measure the temperature of tip electrode 26, targeted tissue, and/or the interface therebetween and provide feedback to the monitoring, recording, or ablation devices described hereinabove. Tip electrode 26 may further include a fluid lumen (not shown) configured as a passageway for irrigation fluid. Tip electrode 26 may be affixed to deflectable distal shaft 18 in a number of ways. For instance, tip electrode 26 may be bonded to an inner radial surface of deflectable distal shaft 18 using an epoxy material. In another embodiment, tip electrode 26 is integral with distal shaft 18.

Still referring to FIG. 1, deflectable distal shaft 18 can be configured for deflection independent of proximal shaft 20 (as shown in phantom lines). Distal shaft 18 is disposed between tip assembly 16 and proximal shaft 20. Distal shaft 18 has a proximal portion 32 and distal portion 34 and may comprise an elongated body extending from proximal portion 32 to distal portion 34 and one or more electrodes 36. The length and diameter of distal shaft 18 can vary according to the application. For example and without limitation, the length of distal shaft 18 can range from about two inches (50.8 millimeters) to about six inches (152.4 millimeters), and the diameter of distal shaft 18 can range from about five French to about twelve French. In an embodiment, the diameter of distal shaft 18 can be about seven French. Although these particular dimensions are mentioned specifically, the dimensions of distal shaft 18 can vary in accordance with various applications.

Electrodes 36 (such as, for example, ring electrodes) may be mounted on or affixed to distal shaft 18. In an embodiment, an active outer surface of each electrode 36 can be configured for exposure to blood and/or tissue. Each electrode 36 may be assembled with distal shaft 18 using any number of known processes. For instance, electrodes 36 may be built into distal shaft 18 using a reflow process. In such a process, electrodes 36 are placed at the appropriate/desired locations on distal shaft 18, and then at least a section of distal shaft 18 is exposed to a heating process in which electrodes 36 and polymeric material of distal shaft 18 become affixed, bonded, or fused together. Sufficiently sized aperture(s) (not shown) may be formed in distal shaft 18 proximate to each electrode 36 in order to allow for wires (not shown) connected to electrodes 36 to be threaded through distal shaft 18. The wires may be pre-coated wires such that they are insulated from each other and other components in device 10. The wires may extend through distal shaft 18, proximal shaft 20, and handle assembly 22 and may be connected to, for example, monitoring and/or recording devices and/or ablation devices associated with or connected to device 10.

Still referring to FIG. 1, elongate proximal shaft 20 has a proximal portion 38 and a distal portion 40. At proximal portion 38, proximal shaft 20 may be connected to handle assembly 22, and at distal portion 40, proximal shaft 20 may be connected to distal shaft 18.

Still referring to FIG. 1, handle assembly 22 is operative to, among other things, effect movement (i.e., deflection) of distal shaft 18. Handle assembly 22 has a distal portion 42 and a proximal portion 44. At its distal portion 42, handle assembly 22 may be coupled to proximal shaft 20 at its proximal portion 38 (disposed within handle assembly 22 and not shown). Proximal portion 44 of handle assembly 22 may be configured to be coupled to a monitoring or recording or ablation device. Handle assembly 22 may comprise an actuator (not shown) that can be selectively manipulated to cause distal shaft 18 to deflect in one or more directions (e.g., up, down, left, and right).

In an embodiment, pull wires 24, 25 (seen in FIGS. 4A-8B) facilitate deflection of distal shaft 18. Pull wires 24, 25 generally may extend through proximal portion 12 to distal portion 14 of device 10. In an embodiment, pull wires 24, 25 may be attached to diametrically opposite locations on an inner radial surface of a pull ring 43 (shown in FIGS. 8A-8B) at distal portion 14 of device 10 by, for example and without limitation, a solder or weld joint. Pull wires 24, 25 then extend proximally from pull ring 43 toward handle assembly 22. Pulling of pull wires 24, 25 via handle assembly 22 during use of device 10 will cause pull ring 43 to tilt or rock, thereby deflecting distal shaft 18. Although device 10 is described and illustrated as including two opposing pull wires 24, 25, it should be noted that device 10 is not limited to two opposing pull wires 24, 25. Rather, device 10 may include a single pull wire arrangement. In other embodiments, device 10 may include more than two pull wires. Pull wires 24, 25 may be formed from a superelastic Nitinol wire, carbon fiber, para-aramid synthetic fiber generally available from DuPont under the brand name KEVLAR®, or other suitable material in accordance with various embodiments.

Figure 2:
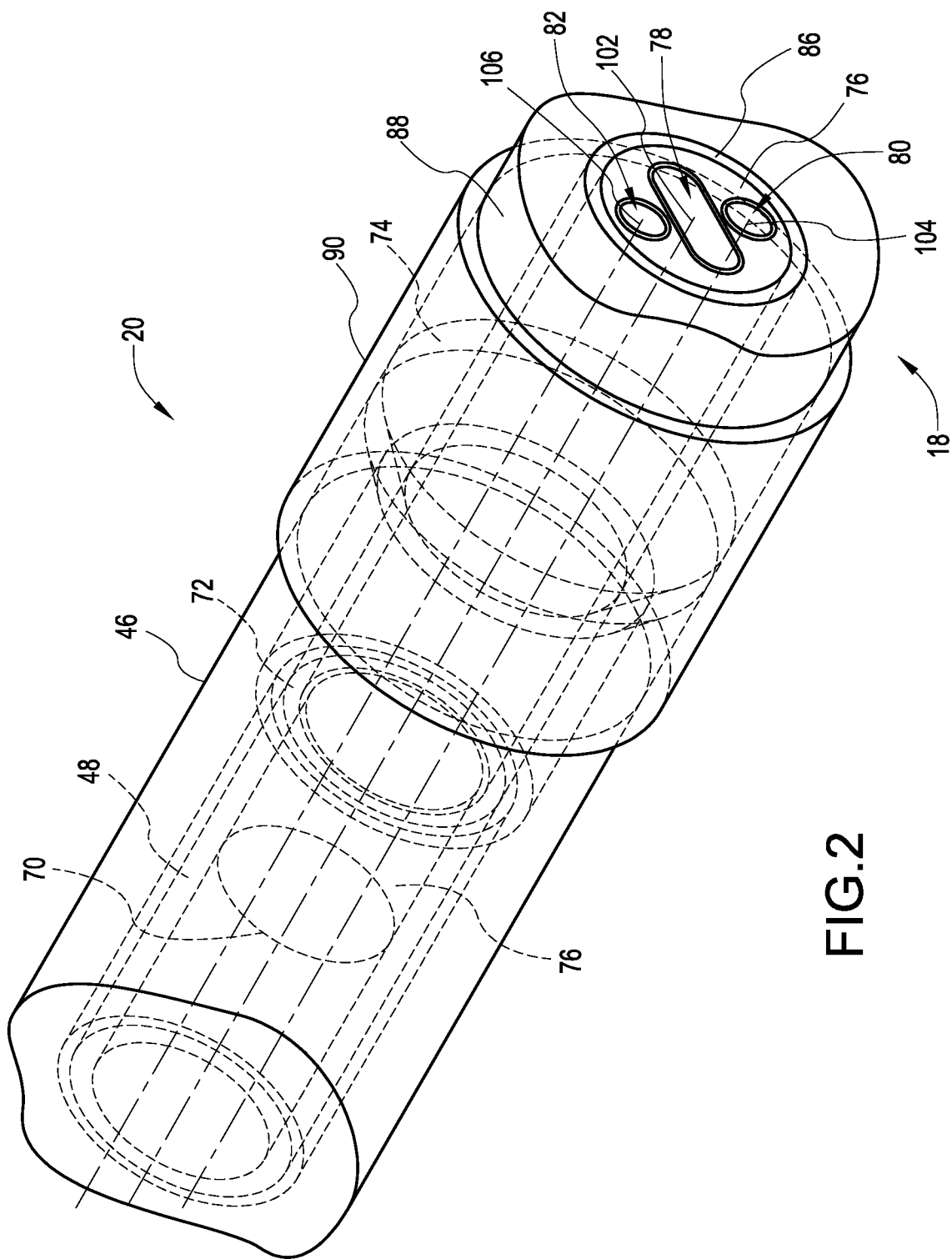
FIG. 2 is a close-up isometric view of the portion indicated as "2" of the medical device illustrated in FIG. 1 in accordance with one embodiment of the present teachings (with some components omitted for clarity).
Figure 4A:
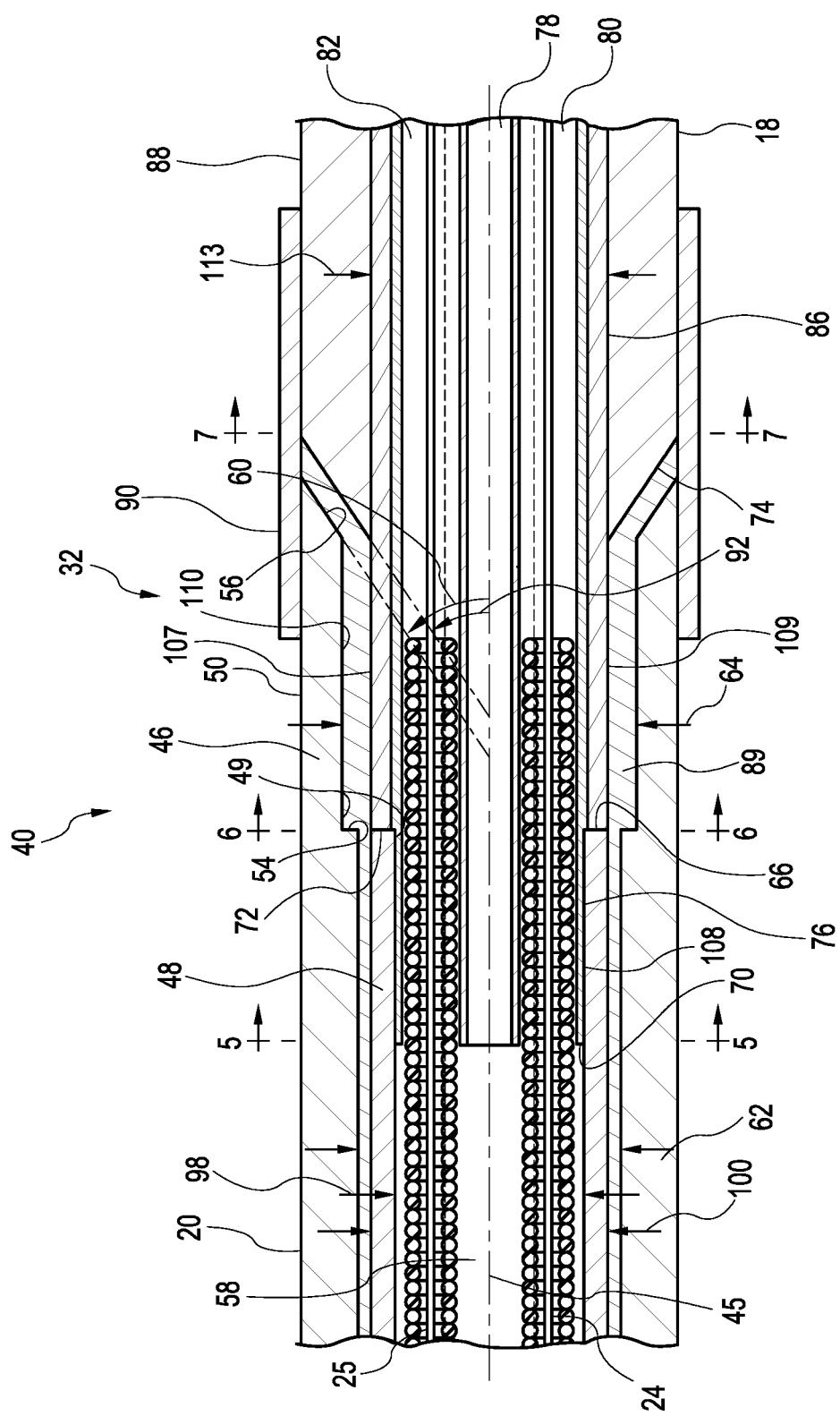
FIG. 4A is a cross-sectional view of the portion of the medical device of FIG. 2 (with some components omitted for clarity).
Figure 4B:
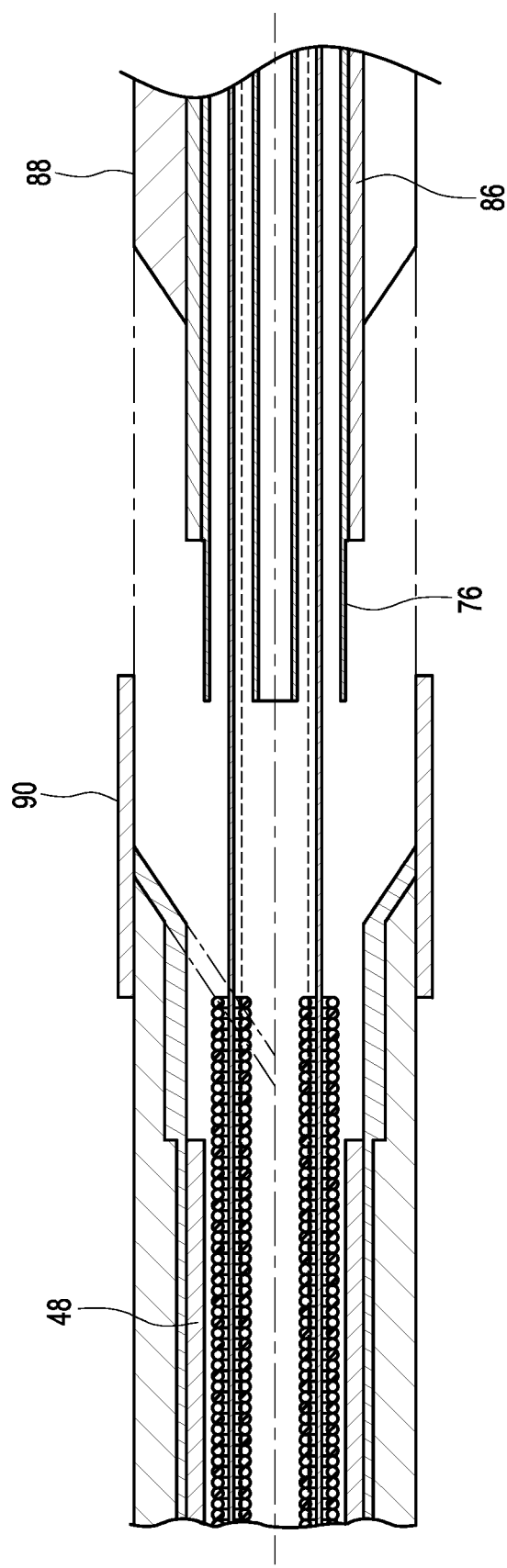
FIG. 4B is a semi-exploded, cross-sectional view of the portion of the medical device of FIG. 2 (with some components omitted for clarity).
Figure 5:
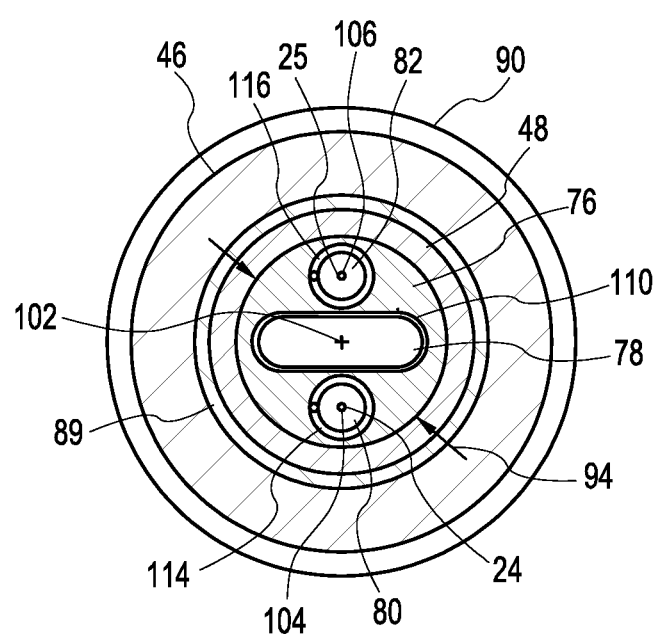
FIG. 5 is a cross-sectional view of the portion of the medical device of FIG. 4A taken along line 5-5.
Figure 6:
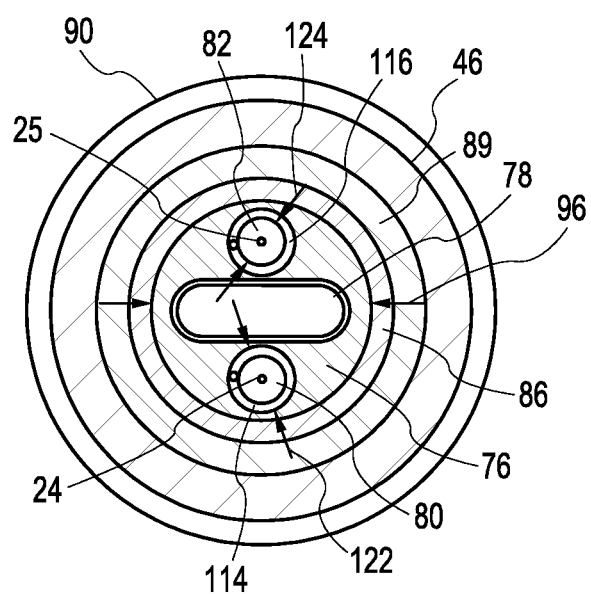
FIG. 6 is a cross-sectional view of the portion of the medical device of FIG. 4A taken along line 6-6.
Figure 7:
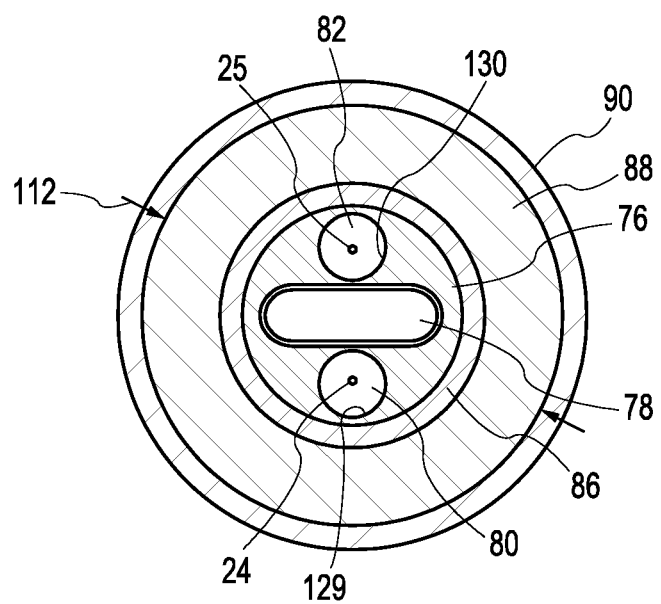
FIG. 7 is a cross-sectional view of the portion of the medical device of FIG. 4A taken along line 7-7.

FIG. 2 is a close-up isometric view of the portion indicated as "2" of the medical device illustrated in FIG. 1 in accordance with one embodiment of the present teachings (with some components omitted for clarity). Specifically, FIG. 2 shows device 10 in an assembled state and generally illustrates the connection points between the various components of device 10, namely between proximal shaft 20 and distal shaft 18. FIG. 3 is an exploded view of the portion of the medical device 10 illustrated in FIG. 2 (with some components omitted for clarity). FIG. 4A is a cross-sectional view of the portion of the medical device 10 of FIG. 2 (with some components omitted for clarity) and generally illustrates the overlapping of certain layers of device 10 defining nested lap joints. FIG. 4B is a semi-exploded, cross-sectional view of the portion of the medical device of FIG. 2 (with some components omitted for clarity). FIGS. 5-7 are various cross-sectional views of the portion of device 10 illustrated in FIG. 4A.

With simultaneous reference to FIGS. 2 and 3, proximal shaft 20 may include an outer layer 46 and a tube or liner 48 disposed within outer layer 46. Distal shaft 18 may include a cylindrical member 76, a braided layer 86, and an outer jacket 88. In an embodiment, these aforementioned components of proximal shaft 20 and distal shaft 18 may be assembled in a layer-by-layer fashion to form nested lap joints, as will be described in more detail below.

Referring particularly to FIGS. 4A-4B, device 10 defines a longitudinal axis 45. Distal portion 40 of proximal shaft 20 may be configured to be coupled with proximal portion 32 of distal shaft 18. Proximal shaft 20 may comprise one layer or a series of layers. As previously discussed, in the illustrated embodiment, proximal shaft 20 comprises outer layer 46, tube or liner 48 disposed within outer layer 46, and a stepped inner surface 49 that extends from proximal portion 38 (FIG. 1) to distal portion 40. In the illustrated embodiment, liner 48 and outer layer 46 define stepped inner surface 49 such that surface 49 comprises an inner surface of liner 48 and a portion of an inner surface of outer layer 46.

Outer layer 46 may have an outer surface 50, an inner edge 54 and a distal edge 56, and a lumen 58. Outer layer 46 may also be generally cylindrical in shape and have a round cross section. It should be understood, however, that outer layer 46 can have various cross-sections, including oval or square, or can have more than one type of cross-sectional shape at different points along its length. Inner edge 54 and distal edge 56 may generally extend in a radial direction. Inner edge 54 is illustrated as extending perpendicular to axis 45, and distal edge 56 is illustrated as extending at an angle 60 relative to axis 45. One of ordinary skill in the art will appreciate, however, that inner edge 54 and distal edge 56 may be at any angle and may not be circumferentially uniform relative to axis 45. For example and without limitation, inner edge 54 and/or distal edge 56 may not be planar but, instead, include a slot that extends proximally. In another embodiment, outer layer 46 may have different lengths along its circumference about axis 45, measured from proximal portion 38 (FIG. 1) to inner edge 54 and/or to distal edge 56. In an embodiment, outer layer 46 may be composed of braided stainless steel wire sandwiched between two layers of polymeric material, such as polyurethane, nylon, or various types of plastic materials (such as polyether block amides offered under the trademark PEBAX® (e.g., 72D Pebax), which is a registered trademark of Arkema France) or any other suitable material. In one embodiment, inner edge 54 may be the point at which one layer of polymeric material ends (i.e., distal of inner edge 54, outer layer 46 is composed of braided wire and only one layer of polymeric material). Regardless of the material used, the material should have the capability to be displaced or to shrink when subjected to a process, such as for example, a heating process that is performed (in accordance with an embodiment). The braided stainless steel wire provides increased stiffness to proximal shaft 20. In the illustrated embodiment, outer layer 46 generally has an inner diameter 62 proximal to inner edge 54 and an inner diameter 64 proximal to distal edge 56. It should be understood, however, that outer layer 46 may have one inner diameter or multiple inner diameters along its length. In one embodiment, proximal shaft 20 is sixty inches in length.

In an embodiment, stepped inner surface 49 defines lumen 58 of proximal shaft 20. Among other things, lumen 58 allows for components of device 10 and fluid to travel between proximal portion 38 and distal portion 40 of proximal shaft 20. As illustrated, lumen 58 extends along axis 45 in the longitudinal direction. In other embodiments, however, proximal shaft 20 may have more than one lumen, and the lumen(s) may be parallel or at an angle to axis 45.

Still referring particularly to FIGS. 4A-4B, liner 48 of proximal shaft 20 has an axial end 66 and may be generally cylindrical in shape. In accordance with an embodiment, liner 48 is disposed along axis 45 within a portion of outer layer 46 of proximal shaft 20. In another embodiment, liner 48 may extend distally outside of outer layer 46. In the illustrated embodiment, axial end 66 of liner 48 is aligned with inner edge 54 of outer layer 46 in the radial direction. One of ordinary skill in the art will understand, however, that axial end 66 of liner 48 may be disposed proximally or distally to inner edge 54. Liner 48 may be composed of a polymeric material, such as polyurethane, nylon, or various types of plastic materials such as polyether block amides offered under the trademark PEBAX®, which is a registered trademark of Arkema France, or any other suitable material. Regardless of the material used, the material should have the capability to be displaced or to shrink when subjected to a process, such as for example, a heating process that is performed (in accordance with an embodiment). The mechanical properties of liner 48 can also be varied, for example, by varying the properties of the polymeric material (e.g., dimension of the cylindrical braid structure and/or durometers of the polymers). Additionally, the mechanical properties of liner 48 can be varied along its length in accordance with some embodiments or can be substantially constant along its entire length in accordance with other embodiments.

Still referring particularly to FIGS. 4A-4B, proximal portion 32 of distal shaft 18 may be configured to be coupled with distal portion 40 of proximal shaft 20. In the illustrated embodiment, a filler or epoxy layer 89 (described in more detail herein below) is sandwiched between portions of proximal shaft 20 and distal shaft 18. As discussed previously, in the illustrated embodiment, distal shaft 18 may extend along longitudinal axis 45, may have proximal edges 70, 72, 74, and may comprise cylindrical member 76 (best seen in FIG. 3), lumens 78, 80, 82 (best seen in FIGS. 5-7), braided layer 86, and outer jacket 88. It should be understood that distal shaft 18 may consist of any number of layers with the same or different materials and have one or several edges at its proximal portion 32. Moreover, in one embodiment, distal shaft 18 is coaxial with proximal shaft 20.

Proximal edges 70, 72, 74 of distal shaft 18 may extend in the radial direction. In one embodiment, proximal edge 74 corresponds in shape to distal edge 56 of proximal shaft 20, and proximal edge 72 of distal shaft 18 corresponds in shape to inner edge 54 of proximal shaft 20 and/or axial end 66 of liner 48. Proximal edges 70 and 72 are illustrated as extending perpendicular to axis 45, and proximal edge 74 is illustrated as extending at an angle 92 relative to axis 45. One of ordinary skill in the art will appreciate, however, that proximal edges 70, 72, 74 may be at any angle and may not be circumferentially uniform. For example and without limitation, proximal edges 70, 72, 74 of distal shaft 18 may not be generally planar but, instead, include a slot or groove that extends in the longitudinal direction and corresponds to a key or protrusion on proximal shaft 20. Moreover, proximal edges 70, 72, 74 of distal shaft 18 may include a key or protrusion extending in the longitudinal direction that corresponds to a slot or groove in proximal shaft 20. In another embodiment, distal shaft 18 may have different lengths (from proximal edge 70, 72, and/or 74 to distal portion 34 shown in FIG. 1) about axis 45 along its circumference.

In the illustrated embodiment, cylindrical member 76 extends from proximal edge 70 of distal shaft 18 to distal portion 34 (FIG. 1) of distal shaft 18 and has two outer diameters: an outer diameter 94 (FIG. 5) between proximal edges 70 and 72 and an outer diameter 96 (FIG. 6) distal of proximal edge 72. However, it should be understood that cylindrical member 76 can have one diameter or more than two diameters. In the illustrated embodiment, proximal edge 70 is proximal to axial end 66 of liner 48 such that a portion of liner 48 overlaps a portion of cylindrical member 76 between proximal edges 70, 72 of distal shaft 18, and axial end 66 of liner 48 is aligned with proximal edge 72 of distal shaft 18 in the radial direction. In an embodiment, the length of cylindrical member 76 between proximal edge 70 and 72 is 0.100 inches. Moreover, in an embodiment, an inner diameter 98 of liner 48 (as best seen in FIGS. 4A-4B) may be slightly larger than or equal to outer diameter 94 (FIG. 5) of cylindrical member 76 such that cylindrical member 76 is snug inside liner 48. In one embodiment, outer diameter 94 of cylindrical member 76 may be 0.064 inches. Furthermore, an outer diameter 100 of liner 48 (as best seen in FIGS. 4A-4B) may be substantially equal to outer diameter 96 (FIG. 6) of cylindrical member 76 in accordance with some embodiments. An adhesive or epoxy may be used between liner 48 and cylindrical member 76 to better secure cylindrical member 76 inside liner 48, such as M-121 epoxy. Although cylindrical member 76 is shown as being cylindrical in shape, it should be understood that member 76 can have a variety of cross-sectional shapes. Moreover, member 76 can have different cross-sectional shapes across its length. In some embodiments, cylindrical member 76 is composed of a thermo-plastic, such as pellethane or polyether block amides offered under the trademark PEBAX®, which is a registered trademark of Arkema France, or any other suitable material. In the illustrated embodiment, lumens 78, 80, 82 are disposed entirely within cylindrical member 76; however, lumens 78, 80, 82 may be disposed (partially or entirely) within other layers of distal shaft 18 in accordance with other embodiments.

Lumens 78, 80, 82 of distal shaft 18 may be configured such that various components or fluids required for performing the particular functionality of device 10 (e.g., recording electrograms, ablation, ultrasound, etc.) are disposed therein. Each lumen 78, 80, 82 may be fully formed or may share common spaces with one another. In accordance with the illustrated embodiment, lumens 78, 80, 82 may be disposed as proximate each other as manufacturally feasible, while allowing each lumen 78, 80, 82 to be fully formed. Depending upon the intended application of device 10, each lumen 78, 80, 82 may extend along an entire length of distal shaft 18 or may extend less than the entire length of distal shaft 18. Each lumen 78, 80, 82 may be formed to have a predetermined cross-sectional profile and shape. Furthermore, each lumen 78, 80, 82 may have various cross-sectional shapes at different points across the length of distal shaft 18.

Referring to FIG. 5, in the illustrated embodiment, cylindrical member 76 has three lumens 78, 80, 82, each with a longitudinal axis 102, 104, 106 (FIG. 2). In other embodiments, distal shaft 18 has one lumen, two lumens, or more than three lumens. In an embodiment, lumens 78, 80, 82 may be generally round or oval in cross-sectional shape and may extend from proximal portion 32 to distal portion 34 (FIG. 1) of distal shaft 18 along their respective axes 102, 104, 106. In an embodiment, lumen 78 may be configured for housing wiring for electrodes 26, 36 (FIG. 1) or for other electrical components and/or for use as an irrigation fluid passageway and the like. Axis 102 of lumen 78 may coincide with axis 45 of device 10 (FIGS. 4A-4B). In the illustrated embodiment, lumen 78 is lined with a liner 110 that serves the purpose of providing a lubricious surface and insulating the components within lumen 78. If provided, liner 110 may be constructed of a polymeric material, such as a polyimide or any other suitable material.

In an embodiment, lumen 80 may be located generally adjacent to or abutting lumen 78 and may be oriented such that its axis 104 is parallel to axis 102 of lumen 78. Lumen 82 may also be located generally adjacent to or abutting lumen 78 and may be oriented such that its axis 106 is parallel to axis 102 of lumen 78. Lumens 80, 82 may be configured to house pull wires 24, 25, respectively, to enable distal shaft 18 to deflect in two or more directions.

Referring back to FIGS. 4A-4B, braided layer 86 of distal shaft 18 has an outer diameter 113 and is configured to provide stiffness and torqueability to distal shaft 18. In the illustrated embodiment, braided layer 86 extends from proximal edge 72 to distal portion 34 (FIG. 1) of distal shaft 18 and circumferentially surrounds a portion of cylindrical member 76. The length and diameter(s) of braided layer 86, however, can vary in accordance with other embodiments. In the illustrated embodiment, outer diameter 113 of braided layer 86 is slightly less than or equal to inner diameter 64 of outer layer 46 such that a portion of braided layer 86 is snug inside a portion of outer layer 46 of proximal shaft 20 between axial end 66 of liner 48 and/or inner edge 54 of outer layer 46 and distal edge 56 of outer layer 46. For example and without limitation, outer diameter 113 of braided layer 86 may be 0.076 inches, and inner diameter 64 of outer layer 46 of proximal shaft 20 may be between 0.076 and 0.078 inches. The length of overlap between layers 46, 86 in the axial direction may be 0.300 inches. Braided layer 86 can be composed of a polymeric material, such as polyurethane, nylon, or various types of plastic materials such as polyether block amides offered under the trademark PEBAX®, which is a registered trademark of Arkema France, or any other suitable material. Regardless of the material used, the material should have the capability to be displaced or to shrink when subjected to a process, such as for example, a heating process that is performed (in accordance with an embodiment). The polymeric material of braided layer 86 may be surrounded by braided stainless steel wire to provide increased stiffness to distal shaft 18. It should be understood that braided layer 86 can be omitted or consist of several layers in accordance with some embodiments. The mechanical properties of braided layer 86 can also be varied, for example, by varying the properties of the cylindrical braid structure(s) and the polymeric material (e.g., dimension of the cylindrical braid structure and/or durometers of the polymers). Additionally, the mechanical properties of braided layer 86 can be varied along its length in accordance with some embodiments or can be substantially constant along its entire length in accordance with other embodiments.

Outer jacket 88 of distal shaft 18 is configured to provide increased stiffness to distal shaft 18. In the illustrated embodiment, outer jacket 88 extends from proximal edge 74 to distal portion 34 (FIG. 1) of distal shaft 18 and circumferentially surrounds a portion of braided layer 86. The length and diameter(s) of jacket, however, can vary in accordance with other embodiments. For example and without limitation, outer jacket 88 may extend distally from proximal edge 70 or 72 of distal shaft 18. The mechanical properties of outer jacket 88 can also be varied along the length of outer jacket 88, for example, by varying the properties of the polymeric material (e.g., durometers of the polymers). For example and without limitation, most proximally, outer jacket 88 may have a segment composed of 65D Pellethane, followed by a segment composed of 55D or 90AE/55D Pellethane. Additionally, the mechanical properties of outer jacket 88 can be substantially constant along its entire length in accordance with other embodiments. It should be understood that outer jacket 88 can be omitted or consist of several layers in accordance with other embodiments.

Furthermore, in the illustrated embodiment, proximal edge 72 is distal of proximal edge 70, and proximal edge 74 is distal of proximal edge 72 in the axial direction such that member 76 extends proximally outside braided layer 86 and outer jacket 88, and braided layer 86 extends proximally outside outer jacket 88. One of ordinary skill in the art would understand, however, that proximal edges 70, 72, 74 may be proximally or distally disposed of one another. Additionally, in the illustrated embodiment device 10 further includes epoxy layer 89 between a portion of braided layer 86 of distal shaft 18 and outer layer 46 of proximal shaft 20 between proximal edges 72, 74 of distal shaft 18. Epoxy layer 89 may also extend in the radial direction between distal edge 56 of proximal shaft 20 and proximal edge 74 of distal shaft 18 and/or proximally of proximal portion 32 of distal shaft 18. In accordance with one embodiment, epoxy layer 89 may be M-121 epoxy. While epoxy layer 89 is configured to improve the bond strength between proximal shaft 20 and distal shaft 18, it should be understood that epoxy layer 89 is optional.

Device 10 may further include a sleeve 90. In the illustrated embodiment, sleeve 90 is disposed circumferentially around a portion of proximal shaft 20 and a portion of distal shaft 18 and may be configured to provide more strength to the joint(s) between proximal shaft 20 and distal shaft 18. In accordance with some embodiments, sleeve 90 may surround proximal and distal shafts 20, 18 at distal edge 56 of proximal shaft 20 and proximal edge 74 of distal shaft 18 and have a length of 0.400 inches. Sleeve 90 may be composed of polymeric material, such as polyurethane, nylon, or various types of plastic materials such as polyether block amides offered under the trademark PEBAX®, which is a registered trademark of Arkema France, or any other suitable material. Regardless of the material used, the material should have the capability to be displaced or to shrink when subjected to a process, such as for example, a heating process that is performed (in accordance with an embodiment).

As best seen in FIGS. 4A-4B, distal shaft 18 may be connected to proximal shaft 20 by two nested lap joints formed between distal shaft 18 and proximal shaft 20. In the illustrated embodiment, cylindrical member 76, braided layer 86, and outer jacket 88 define a stepped outer surface 107 of distal shaft 18. Outer surface 107 includes steps 108, 109 extending in the axial direction. Step 108 may extend from proximal edge 70 to proximal edge 72. Step 109 may extend from proximal edge 72 to proximal edge 74. In the illustrated embodiment, a portion of liner 48 of proximal shaft 20 overlaps step 108 of distal shaft 18 in the radial direction to form a lap joint, and outer layer 46 of proximal shaft 20 nests this lap joint at edges 66, 72. Moreover, in the illustrated embodiment, inner surface 49 of proximal shaft 20 includes a step 110 extending in the axial direction from axial end 66 and/or inner edge 54 to distal edge 56. In an embodiment, inner step 110 of proximal shaft 20 overlaps step 109 of distal shaft 18 in the radial direction to form another lap joint, and sleeve 90 nests this lap joint at edges 56, 74. Although the nested lap joints are illustrated as extending circumferentially about axis 45, one of ordinary skill in the art will understand that the joints can instead extend partially about axis 45 (e.g., via slots and corresponding keys in proximal shaft 20 and distal shaft 18). The lap joints can be nested within each other to provide greater joint strength and to more effectively spread the loads and stresses across the various layers of device 10. Moreover, in the illustrated embodiment, the nested lap joints are staggered in the axial direction to spread the loads and stresses across the various layers of device 10 and to reduce the peak force experienced by any individual material. However, one of ordinary skill in the art will understand and appreciate that only one joint could be used, that nesting of the joints is optional, and that the lap joints do not have to be staggered in the axial direction in accordance with other embodiments.

Figure 8A:
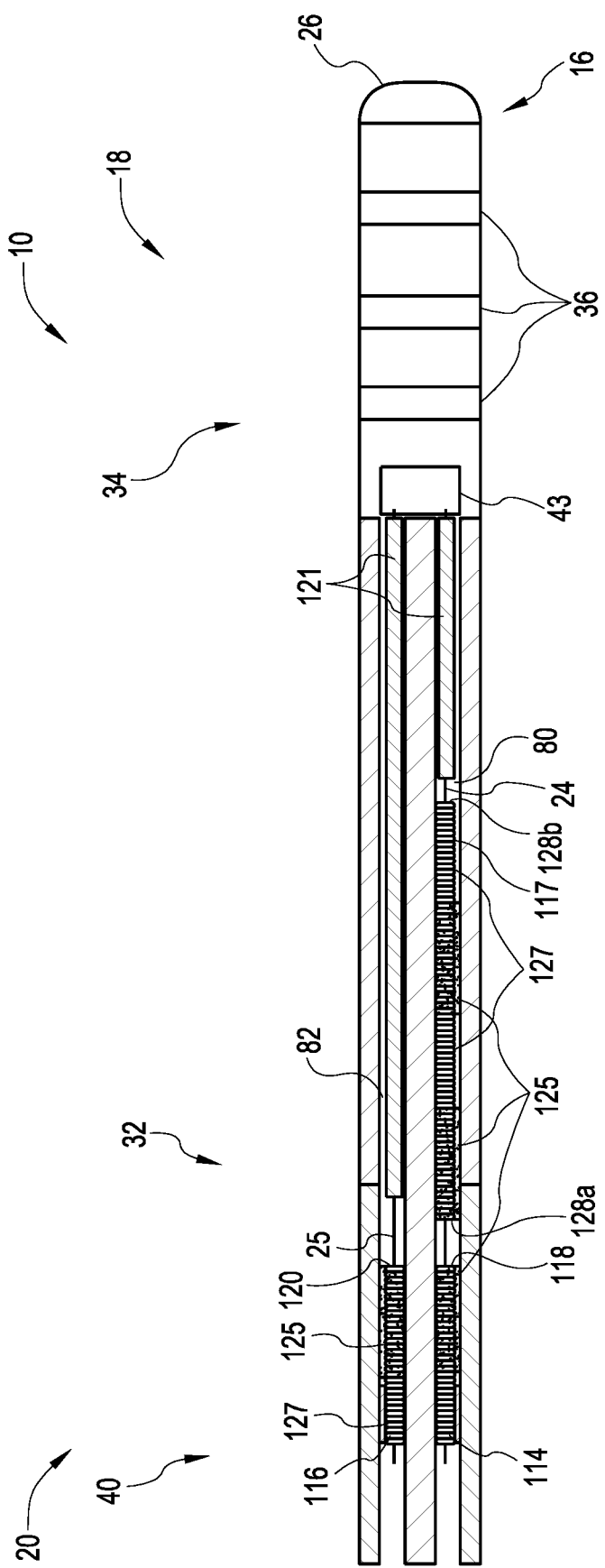
FIG. 8A is a schematic view of a distal portion of the medical device of FIG. 1 in accordance with another embodiment of the present teachings.

FIG. 8A is a schematic view of a portion of the medical device of FIG. 1 in accordance with another embodiment of the present teachings. As illustrated, device 10 can further include compression coils 114, 116 disposed around pull wires 24, 25 in the one or more lumens of proximal shaft 20 that extend from proximal portion 38 (FIG. 1) to distal portion 40 of proximal shaft 20 or slightly into proximal portion 32 of distal shaft 18. Device 10 may also include one or more spring packs 117 disposed around pull wire(s) 24, 25 in lumens 80, 82 of distal shaft 18. Compression coils 114, 116 and/or spring pack 117 may be configured to provide the desired mechanical property of resisting compression during use as described in more detail in the '124 Application. Because compression coils 114, 116 and spring pack 117 are generally not easily compressible, tension on pull wires 24, 25 will not translate into compressive tension on proximal shaft 20 and/or distal shaft 18. Compression coils 114, 116 and spring pack 117 are therefore configured to help assure that proximal shaft 20 and/or distal shaft 18 does not bend as a result of tension on pull wires 24, 25 and that rotational control of device 10 is not adversely affected when pull wires 24, 25 are under tension. In an embodiment, each of compression coils 114, 116 and/or spring pack 117 is tightly wound so it can bend, but is generally non-compressible. While pull wires 24, 25 may extend from handle assembly 22 (FIG. 1) to pull ring 43, compression coils 114, 116 may generally extend only through proximal shaft 20 and perhaps slightly into proximal portion 32 of distal shaft 18, in accordance with some embodiments. Compression coils 114, 116 can extend the entire length of proximal shaft 20 in accordance with some embodiments. Each of the compression coils 114, 116 comprises a distal end 118, 120. The distance between distal end 118, 120 of coils 114, 116 and pull ring 43 may generally affect the curvature of distal shaft 18. As best seen in FIG. 6, an outer diameter 122 of compression coils 114, 116 may be about 0.015 inches (0.38 millimeters) to about 0.030 inches (0.76 millimeters), and an inner diameter 124 of compression coils 114, 116 may be about 0.004 inches (0.10 millimeters) to about 0.015 inches (0.38 millimeters). Each of compression coils 114, 116 can comprise stainless steel in accordance with an embodiment. Where not disposed within a spring pack 117, pull wires 24, 25 may be surrounded by a tube 121 made of a material, such as PTFE.

In accordance with some embodiments, compression coils 114, 116 and/or spring pack 117 may include fused areas 125 with a fused coil pitch and unfused areas 127 with an unfused coil pitch. By allowing compression coils 114, 116 and/or spring pack 117 to have unfused areas 127 and fused areas 125 within proximal shaft 20 and/or distal shaft 18, proximal shaft 20 and/or distal shaft 18 may be configured to provide pushability and torqueability for device 10, while no longer being necessary to address shaft compression and/or snaking. Unfused areas 127 are configured to provide strain relief to device 10 and may be located between fused areas 125, at a proximal end 128a and/or a distal end 128b of spring pack 117, at proximal ends (not shown) of compression coils 114, 116, and/or at distal ends 118, 120 of compression coils 114, 116. In an embodiment, the coil pitch at proximal and/or distal ends of compression coils 114, 116 and/or spring pack 117 may have a greater coil pitch than the coil pitch(es) disposed therebetween to reduce stress at the proximal and distal ends of the compression coils 114, 116 and/or spring pack 117. By separating compression coils 114, 116 from proximal shaft 20 and distal shaft 18 themselves, device 10 can undergo bench testing for assessing deflection of device 10 prior to formation of device 10 through a reflow process as described in more detail hereinbelow (and in the '124 Application). Moreover, by not fixedly attaching compression coils 114, 116 to device 10 or components thereof, device 10 may exhibit improved ease of assembly. Although compression coils 114, 116 and spring pack 117 are mentioned as having two coil pitches (fused coil pitch and unfused coil pitch), compression coils 114, 116 and/or spring pack 117 may have one coil pitch or multiple coil pitches throughout their respective lengths in accordance with other embodiments.

Referring to FIG. 8A, fused areas 125 of compression coils 114, 116 and/or spring pack 117 may be fused to or embedded within inner surfaces 129, 130 (FIG. 7) of lumens 80, 82 of cylindrical member 76 and/or inner surface 49 of proximal shaft 20 (such as, for example and without limitation, an inner surface of liner 48 or an inner wall of the polymeric material of outer layer 46 of proximal shaft 20, as seen in FIGS. 4A-4B). Moreover, the location of fused areas 125 relative to pull ring 43 disposed in distal portion 32 of distal shaft 18 may generally affect the curvature of distal shaft 18. In the illustrated embodiment in FIG. 8A, pull wire 24 may exhibit a first radius of curvature upon tension, while pull wire 25 may exhibit a second radius of curvature upon tension. In the illustrated embodiment in FIG. 8A, the first and second radii of curvature exhibited by pull wires 24, 25 upon tension are different. It should be understood that pull wires 24, 25 can be configured to have any curvature known in the art and that such curvature can be configured by fusing various portion(s) of compression coils 114, 116 and/or spring pack 117 along their respective lengths. In accordance with some embodiments, fused areas 125 may have a fused coil pitch that is smaller than an unfused coil pitch of unfused areas 127 of compression coils 114, 116. In an embodiment, proximal portion 38 (FIG. 1) of proximal shaft 20 is filled with adhesive to prevent coils 114, 116 from moving more proximally. In accordance with some embodiments, the proximal ends of each of compression coils 114, 116 is not fixedly attached to handle assembly 22, but instead abuts or stops at or is constrained by an axial end surface (e.g., of an adhesive) of proximal portion 38 (FIG. 1) of proximal shaft 20.

In accordance with other embodiments, areas 125 of compression coils 114, 116 and/or spring pack 117 (to be fused) may each be circumferentially surrounded by and/or fused to a jacket of polymeric material, and the jacket may be fused to proximal shaft 20 and/or distal shaft 18 (as described hereinabove). In some embodiments, prior to fusion with proximal shaft 20 and/or distal shaft 18, fused areas 125 may be stretched, and then the jackets may be heated such that the material of the jacket melts and flows in between the stretched coil gaps of compression coils 114, 116 and/or spring pack 117. Use of a jacket may aid in subsequent fusion with proximal shaft 20 and/or distal shaft 18. Flowing the jacket material into the stretched coil gaps may prevent the material of proximal shaft 20 or distal shaft 18 from sinking into the coil gaps causing sink holes. The jackets can be composed of polymeric material, such as polyurethane, nylon, or various types of plastic materials such as polyether block amides offered under the trademark PEBAX®, which is a registered trademark of Arkema France, or any other suitable material. Regardless of the material used, the material should have the capability to be displaced or to shrink when subjected to a process, such as for example, a heating process that is performed (in accordance with an embodiment).

Referring to FIG. 8B, device 10' includes compression coils 114', 116' with fused areas 125' and unfused areas 127'. In this illustrated embodiment, compression coils 114', 116' are generally the same length (i.e., their respective distal ends 118', 120' are aligned in the radial direction) such that pull wires 24', 25' generally exhibit the same radius of curvature upon tension.

Figure 9:
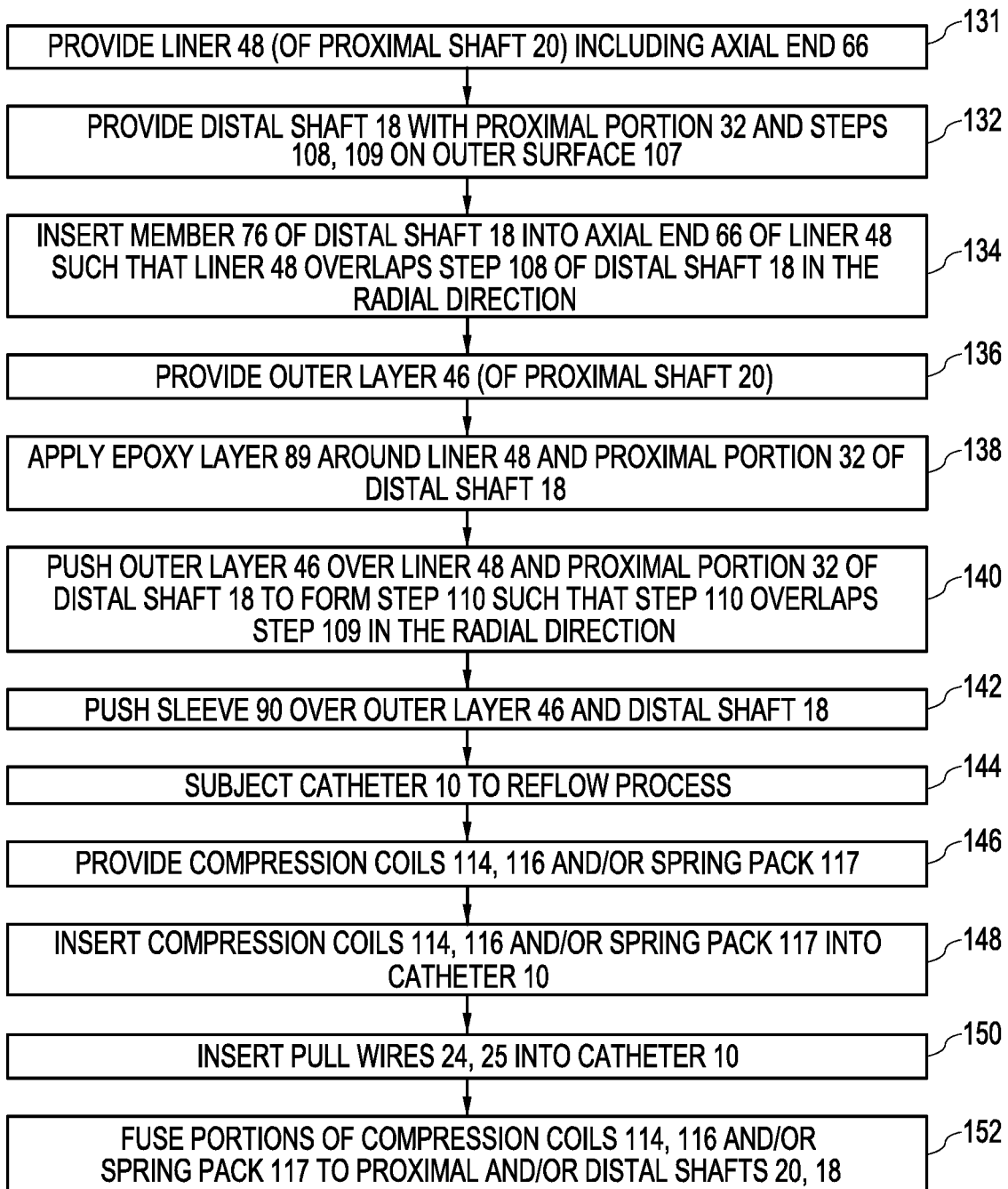
FIG. 9 is a flow chart diagram of a method for fabricating the medical device of FIG. 1 in accordance with another embodiment of the present teachings.

With reference to FIG. 9, a method of fabricating device 10 will now be described. The method may begin with the process 131 of providing liner 48. As set forth hereinabove, liner 48 may have axial end 66.

The method may continue with the process 132 of providing distal shaft 18 with proximal portion 32 and steps 108, 109 on outer surface 107 (see FIGS. 4A-4B). Process 132 may include several subprocesses. In accordance with one embodiment, process 132 may begin with the process of providing cylindrical member 76 with lumens 78, 80, 82, the process of which is discussed in more detail in the '124 Application. Then, braided layer 86 may be formed by braiding a wire around an Acetyl core and thereafter removing the core. Next, formed braided layer 86 may be slid over cylindrical member 76. Thereafter, outer jacket 88 may be slid over braided layer 86. Next, some of the material of braided layer 86 and outer jacket 88 (and optionally a portion of cylindrical member 76) may be removed or machined off to form the stepped outer surface 107 (and proximal edges 70, 72, 74). Moreover, outer jacket 88 may be removed distally of proximal edge 72 to form proximal edge 74.

The method may continue with the process 134 of inserting cylindrical member 76 into axial end 66 of liner 48 such that liner 48 overlaps step 108 of distal shaft 18 in the radial direction, thus, forming a lap joint. Process 134 may include several subprocesses. In certain embodiments, an adhesive or epoxy (not shown) may be applied to one or both of an inner surface of liner 48 and step 108 of cylindrical member 76. In an embodiment, axial end 66 of liner 48 abuts and/or aligns with proximal edge 72 of distal shaft 18.

The method may continue with the process 136 of providing outer layer 46 of proximal shaft 20. Process 136 may include several subprocesses. In one embodiment, outer layer 46 is formed by coating an Acetyl plastic core with a polymeric material using extrusion equipment. Wire may then be braided around the coated core. Thereafter, another layer of polymer or plastic coats the braid. Finally, the core is removed to produce a hollow braided shaft.

The method may continue with the process 138 of applying an epoxy layer 89 around liner 48 and proximal portion 32 of distal shaft 18. In some embodiments, epoxy layer 89 may be applied between proximal edges 72, 74 of distal shaft 18. In accordance with one embodiment, epoxy layer 89 may be M-31 epoxy.

The method may continue with the process 140 of pushing outer layer 46 over liner 48 and proximal portion 32 of distal shaft 18 to form step 110 such that step 110 overlaps step 109 in the radial direction, thus nesting the lap joint formed in process 134 and forming another lap joint. Epoxy layer 89 may extend partially in the radial direction between distal edge 56 of proximal shaft 20 and proximal edge 74 of distal shaft 18, as a result of this process 140. In an embodiment, distal edge 56 of outer layer 46 abuts and/or aligns with proximal edge 74 of distal shaft 18. Moreover, in an embodiment, inner edge 54 of outer layer 46 is radially aligned with axial end 66 of liner 48.

The method may continue with the process 142 of pushing sleeve 90 over proximal shaft 20 and distal shaft 18, thus, nesting the lap joint formed in process 140. In an embodiment, sleeve 90 circumferentially surrounds proximal shaft 20 and distal shaft 18 at distal edge 56 of proximal shaft 20 and proximal edge 74 of distal shaft 18.

The method may continue with the process 144 of subjecting device 10 to a reflow process, the details of which are discussed in the '124 Application.

The method may continue with the process 146 of providing compression coils 114, 116 and/or spring pack 117. Process 146 may include several subprocesses. In one embodiment, compression coils 114, 116 and spring packs 117 are pre-made to have multiple coil pitches throughout their lengths, for example and without limitation, a fused coil pitch and an unfused coil pitch. In another embodiment, jackets are slid over the portions of compression coils 114, 116 to be fused (denoted as 125), as described in more detail hereinabove in connection with FIGS. 8A-8B. Then, the portions that are to be fused (125) are stretched (forming the fused coil pitch) and heated such that the material of the jacket melts and flows in between the individual coil sections, thus, retaining the fused coil pitch. Flowing the jacket material into the stretched coil gaps may prevent the material of proximal shaft 20 or distal shaft 18 (in subsequent fusion) from sinking into the coil gaps causing sink holes.

The method may continue with the process 148 of inserting compression coils 114, 116 and/or spring pack 117 into device 10. In an embodiment, compression coils 114, 116 are disposed within proximal shaft 20 and may extend slightly into distal shaft 18. In an embodiment, spring pack 117 is disposed within distal shaft 18.

The method may continue with the process 150 of inserting pull wires 24, 25 into device 10. In an embodiment, pull wires 24, 25 extend through lumen(s) of proximal shaft 20, lumens 80, 82 of distal shaft 18 (respectively), compression coils 114, 116 (respectively), and pull wire 24 may extend through spring pack 117 (see FIG. 8A).

The method may continue with the process 152 of fusing portions 125 of compression coils 114, 116 and/or spring pack 117 to proximal shaft 20 and/or distal shaft 18. In an embodiment, process 152 comprises selectively heating portions 125 using an energy source. In accordance with one embodiment, such fusion is accomplished by using RF energy. For example and without limitation, an RF energy source is placed around device 10 in the area to be fused. The focused RF energy (in the form of electro-magnetic fields) passes through the non-conductive, non-RF-absorbent materials (i.e., outer layer 46 and liner 48 of proximal shaft 20 and member 76, braided layer 86, and outer jacket 88 of distal shaft 18) and, thus, selectively targets the conductive, RF-absorbent materials (i.e., compression coils 114, 116 and spring pack 117). The RF energy induces a current in compression coils 114, 116 and/or spring pack 117 and, thus, causes them to heat up. The material in close proximity to compression coils 114, 116 and/or spring pack 117 (e.g., pellethane of cylindrical member 76) is heated as a result, melts, and flows within and around the individual coil/spring sections. The material is permitted to cool, thus, resulting in the embedding or fusing of fused areas 125 within proximal shaft 20 and/or distal shaft 18. Process 152 allows for compression coils 114, 116 and/or spring pack 117 to become fused to proximal shaft 20 and/or distal shaft 18 without making any physical contact and without making any holes in device 10. Moreover, process 152 allows for fusing without causing any physical changes to outer layer 46 of proximal shaft 20 and braided layer 86 and outer jacket 88 of distal shaft 18. Additionally, the process 152 is highly precise and easily controllable (e.g., within ±0.1 inches). Although processes 146, 148, 150 are described as occurring after process 152 of subjecting device 10 to a reflow process, one of ordinary skill in the art will understand that such processes can occur in several different orders in accordance with other embodiments. Additionally, it should be understood that other conductive elements of device 10 can be fused or embedded to a layer(s) within device 10, such as thermal sensors.

Figure 10A:
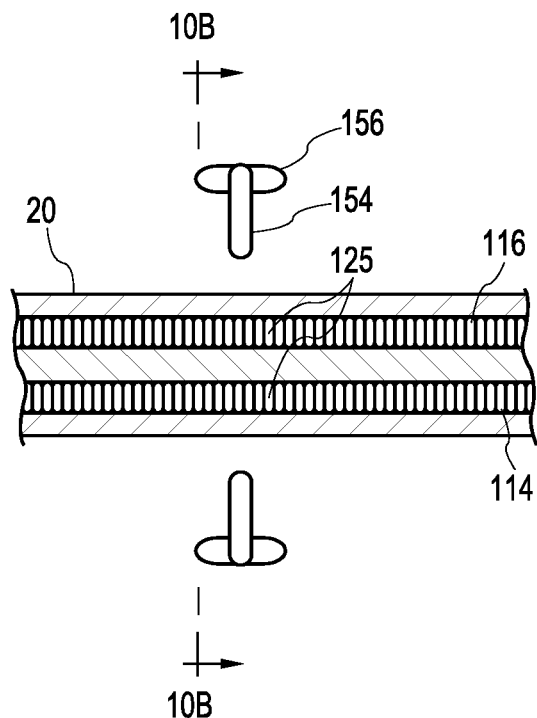
FIG. 10A is a schematic view of a portion of the medical device of FIG. 1 in relation to an RF coil illustrating an embodiment of the method of FIG. 9.
Figure 10B:
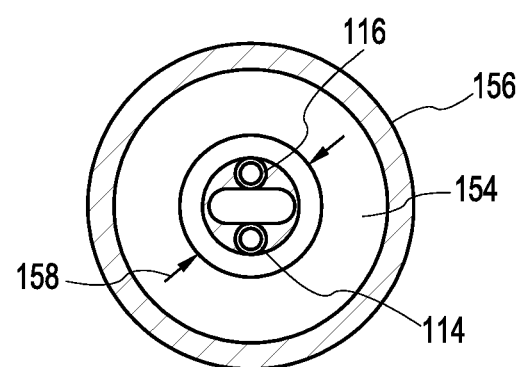
FIG. 10B is a cross-sectional view of the portion of the medical device of FIG. 10A taken along line 10B-10B.

FIG. 10A is a schematic view of a distal portion of the medical device of FIG. 1 illustrating an embodiment of the method of FIG. 9. FIG. 10B is a cross-sectional view of the distal portion of the medical device of FIG. 10A taken along line 10B-10B. Specifically, FIGS. 10A and 10B show an embodiment of the process 152 of fusing portions 125 of compression coils 114, 116 and/or spring pack 117 to proximal shaft 20 and/or distal shaft 18. As illustrated, RF energy may be applied using an RF coil 154 with an intensifier 156. Referring to FIG. 10B, RF coil 154 may be circular in shape with an inner diameter 158. Inner diameter 158 may be large enough such that coil 154 may circumferentially surround device 10 without contacting device 10. One of ordinary skill in the art will understand that other RF tools with various shapes may be used to apply RF energy (or another energy that selectively heats compression coils 114, 116 and spring pack 117) in accordance with other embodiments.

In one embodiment, device 10 is fabricated using the method described in connection with FIG. 9. In another embodiment, device 10 is fabricated using process 152 of fusing portions 125 of compression coils 114, 116 and/or spring pack 117 to proximal shaft 20 and/or distal shaft 18, but does not include the nested lap joint(s) described hereinabove. In yet another embodiment, device 10 is fabricated to include the nested lap joint(s) but is not fabricated according to process 152 of fusing portions 125 of compression coils 114, 116 and/or spring pack 117 to proximal shaft 20 and/or distal shaft 18. One of ordinary skill in the art will understand that each improvement disclosed herein is not necessary to the other in order to function and improve device 10.

Although only certain embodiments have been described above with a certain degree of particularity, those skilled in the art could make numerous alterations to the disclosed embodiments without departing from the scope of this disclosure. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of embodiments. Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the spirit of the disclosure.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While one or more particular embodiments have been shown and described, it will be understood by those of skill in the art that various changes and modifications can be made without departing from the spirit and scope of the present teachings.

What is claimed is:

1. A medical device for diagnosis or treatment of tissue in a body, comprising:
    a first shaft including
        an inner surface, and
        a first shaft axial end;
    a second shaft including a second shaft axial end; and
    a conductive element including a fused portion, the fused portion couples the first shaft axial end of the first shaft to the second shaft axial end of the second shaft;
    wherein the conductive element is a spring pack with a longitudinal axis, the spring pack including
        the fused portion with a fused coil pitch, and
        an unfused portion with at least one unfused coil pitch, and the fused coil pitch is greater than the at least one unfused coil pitch.

2. The device of claim 1, wherein the first shaft includes a distal end, the second shaft extends distally of the distal end of the first shaft, and the conductive element is disposed at least partially in the second shaft.

3. The device of claim 1, wherein the fused portion of the spring pack is disposed between a first and second axial end of the spring pack, and the spring pack further includes at least one strain-relief region.

4. The device of claim 1, wherein the inner surface of the first shaft is configured and arranged to form the fused portion by selectively heating at least a portion of the conductive element using an energy source.

5. The device of claim 4, wherein the energy source is an electro-magnetic field.

6. The device of claim 4, wherein the energy source is a radio-frequency energy, and the inner surface of the first shaft is further configured and arranged to create the fused portion by selectively heating the portion of the conductive element by applying a current.

7. The device of claim 1, wherein the first shaft further includes a tube with a tube axial end and an outer layer disposed around the tube, the outer layer includes an outer layer axial end corresponding to the first shaft axial end, and an inner edge of the first shaft corresponds to at least one of the tube axial end and an outer layer inner edge axially offset from the outer layer axial end and extending in the radial direction.

8. The device of claim 7, wherein the outer layer inner edge is aligned with the tube axial end in the radial direction.

9. The device of claim 1, further comprising a filler disposed between the first shaft and the second shaft.

10. The device of claim 1, further comprising a sleeve disposed around the first shaft and the second shaft.

* * * * *